US007400398B2

(12) United States Patent
Stedman (10) Patent No.: US 7,400,398 B2
(45) Date of Patent: Jul. 15, 2008

(54) REMOTE EMISSIONS SENSING SYSTEM AND METHOD INCORPORATING SPECTRAL MATCHING BY DATA INTERPOLATION

(75) Inventor: Donald H. Stedman, Denver, CO (US)

(73) Assignee: Environmental Systems Products Holdings Inc., East Granby, CT (US)

( * ) Notice: Subject to any disclaimer, the term of this patent is extended or adjusted under 35 U.S.C. 154(b) by 114 days.

(21) Appl. No.: 11/430,106

(22) Filed: May 9, 2006

(65) Prior Publication Data

US 2007/0263213 A1 Nov. 15, 2007

(51) Int. Cl.
*G01N 21/31* (2006.01)
*G01J 3/42* (2006.01)
(52) U.S. Cl. ..................... 356/326; 356/438
(58) Field of Classification Search ................. 356/326, 356/438
See application file for complete search history.

(56) References Cited

U.S. PATENT DOCUMENTS

| | | | | |
|---|---|---|---|---|
| 3,696,247 | A * | 10/1972 | McIntosh et al. | 250/339.07 |
| 4,060,326 | A * | 11/1977 | Tirabassi et al. | 356/328 |
| 4,924,095 | A * | 5/1990 | Swanson, Jr. | 250/338.5 |
| 5,070,246 | A * | 12/1991 | Durham et al. | 250/373 |
| 5,210,702 | A | 5/1993 | Bishop et al. | |
| 5,229,838 | A * | 7/1993 | Ganz et al. | 356/328 |
| 5,252,828 | A * | 10/1993 | Kert et al. | 250/339.13 |
| 5,303,165 | A * | 4/1994 | Ganz et al. | 356/319 |
| 5,319,199 | A | 6/1994 | Stedman et al. | |
| 5,343,043 | A | 8/1994 | Johnson | |
| 5,371,367 | A * | 12/1994 | DiDomenico et al. | 250/338.5 |
| 5,401,967 | A * | 3/1995 | Stedman et al. | 250/338.5 |
| 5,418,366 | A * | 5/1995 | Rubin et al. | 250/338.5 |
| 5,489,777 | A * | 2/1996 | Stedman et al. | 250/338.5 |
| 5,498,872 | A * | 3/1996 | Stedman et al. | 250/338.5 |
| 5,583,765 | A * | 12/1996 | Kleehammer | 701/1 |
| 5,589,629 | A * | 12/1996 | Quinn | 73/23.31 |
| 5,591,975 | A * | 1/1997 | Jack et al. | 250/338.5 |
| 5,644,133 | A | 7/1997 | Didomenico et al. | |
| 5,693,872 | A * | 12/1997 | Quinn | 73/23.31 |
| 5,719,396 | A | 2/1998 | Jack et al. | |

(Continued)

FOREIGN PATENT DOCUMENTS

EP 0 692 703 A1 1/1996

(Continued)

OTHER PUBLICATIONS

Snider, D.; Shanks, R.; Cole, R.; Hudson, M.K.; "Inexpensive photodiode arrays for use in rocket plume and hot source monitoring and diagnostics"; 2003, Measurement Science and Technology, vol. 14, p. 1725-1733.*

*Primary Examiner*—Gregory J Toatley, Jr.
*Assistant Examiner*—Bryan Giglio
(74) *Attorney, Agent, or Firm*—Pillsbury Winthrop Shaw Pittman, LLP (57) ABSTRACT

A system and method for correcting for "wavelength drift" in an RES system. One advantage provided by the invention includes the ability to correct for offset amounts of "wavelength drift" that are not divisible by an integer number of pixels (e.g., fraction pixel offset amounts) in an optical detector used in the RES system. Correction of fractional pixel offset amounts may enhance spectral matching, enable substantially continuous calibration of an RES system, and/or other benefits.

19 Claims, 8 Drawing Sheets

U.S. PATENT DOCUMENTS

| | | | |
|---|---|---|---|
| 5,724,268 A * | 3/1998 | Sodickson et al. | 702/23 |
| 5,726,450 A | 3/1998 | Peterson et al. | |
| 5,771,094 A * | 6/1998 | Carter et al. | 356/326 |
| 5,797,682 A * | 8/1998 | Kert et al. | 374/123 |
| 5,812,249 A | 9/1998 | Johnson et al. | |
| 5,831,267 A * | 11/1998 | Jack et al. | 250/338.5 |
| 5,850,623 A * | 12/1998 | Carman et al. | 702/28 |
| 5,877,862 A | 3/1999 | Nelson et al. | |
| 6,067,156 A * | 5/2000 | Slater et al. | 356/301 |
| 6,137,104 A | 10/2000 | Webb et al. | 250/226 |
| 6,230,087 B1 | 5/2001 | Didomenico et al. | |
| 6,307,201 B1 * | 10/2001 | Didomenico et al. | 250/339.13 |
| 6,384,903 B1 * | 5/2002 | Fuller | 356/4.01 |
| 6,455,851 B1 * | 9/2002 | Lord et al. | 250/338.5 |
| 6,560,545 B2 * | 5/2003 | Stedman et al. | 702/28 |
| 6,608,677 B1 * | 8/2003 | Ray et al. | 356/301 |
| 6,671,630 B2 | 12/2003 | Stedman et al. | |
| 6,701,256 B2 * | 3/2004 | Stedman et al. | 702/24 |
| 6,723,989 B1 | 4/2004 | Didomenico et al. | |
| 6,803,577 B2 * | 10/2004 | Edner et al. | 250/339.09 |
| 6,876,448 B2 * | 4/2005 | Imura et al. | 356/326 |
| 6,983,639 B1 | 1/2006 | DiDomenico et al. | |
| 7,002,143 B2 * | 2/2006 | Parker et al. | 250/282 |
| 7,016,789 B2 * | 3/2006 | Stedman et al. | 702/24 |
| 7,049,595 B2 * | 5/2006 | Kansakoski et al. | 250/338.5 |
| 7,141,793 B2 * | 11/2006 | Johnson et al. | 250/338.5 |
| 7,164,132 B2 * | 1/2007 | Didomenico et al. | 250/338.5 |
| 7,275,414 B2 * | 10/2007 | Nelson et al. | 73/23.31 |
| 2002/0015151 A1 | 2/2002 | Gorin | 356/303 |
| 2002/0052698 A1 * | 5/2002 | Didomenico et al. | 702/31 |
| 2003/0089854 A1 | 5/2003 | Shifflett et al. | |
| 2003/0120434 A1 * | 6/2003 | DiDomenico et al. | 702/22 |
| 2004/0155191 A1 | 8/2004 | Stedman et al. | |
| 2005/0197794 A1 * | 9/2005 | Full | 702/100 |
| 2005/0207943 A1 * | 9/2005 | Puzey | 422/82.05 |
| 2006/0047445 A1 * | 3/2006 | Williams et al. | 702/30 |

FOREIGN PATENT DOCUMENTS

| | | |
|---|---|---|
| WO | WO 01/84097 | 11/2001 |

* cited by examiner

REMOTE EMISSIONS SENSING SYSTEM AND METHOD INCORPORATING SPECTRAL MATCHING BY DATA INTERPOLATION

FIELD OF THE INVENTION

The invention relates generally to remote emissions sensing systems, and more particularly to a remote emissions sensing system and method incorporating spectral matching by data interpolation to correct for "wavelength drift" in an optical detector.

BACKGROUND OF THE INVENTION

Remote emissions sensing systems (hereinafter "RES systems") for detecting the concentrations of one or more gases in an exhaust plume of a motor vehicle are known. Conventional systems are configured to direct electromagnetic radiation through an exhaust plume of a passing vehicle, and monitor the intensity of the electromagnetic radiation received at a detector after the electromagnetic radiation has passed through the plume. As the electromagnetic radiation passes through the plume, gases within the plume may absorb the radiation within specific wavelength absorption bands that correspond to the particular gases present. Based on the amount of light transmitted and/or absorbed by the exhaust plume within the specific wavelength absorption bands, the concentrations of one or more of the gases may be determined.

Typically, to monitor the amount of radiation transmitted and/or absorbed within specific wavelength absorption bands, a conventional RES system may spatially separate the electromagnetic radiation into a spectrum and direct the spectrum incident on a sensor array, such as a diode array or other sensor array. A wavelength scale may be used to associate signals from the pixels (e.g., the individual diodes) with predictions of the wavelengths of radiation that may be received by the pixels, thereby enabling the intensities of radiation within particular wavelength bands to be determined. However, one source of inaccuracy in conventional systems may include a phenomenon known as "wavelength drift." "Wavelength drift" is a phenomenon in which the spectrum of spatially arranged electromagnetic radiation incident on the sensor may wander such that the wavelength ranges of the electromagnetic radiation received by the sensor pixels vary over time. For example, ambient conditions (e.g., temperature, pressure, etc.), mechanical instability, and/or other factors may cause "wavelength drift" within the detector. As the portion of the spectrum incident on each of the pixels in the sensor array wanders, the association of the signals generated by the pixels with particular wavelengths, or wavelength ranges, by the wavelength scale may shift.

Current methods for correcting for "wavelength drift" in RES systems tend to be inefficient and/or inaccurate. For example, a typical approach for calibrating for "wavelength drift" may include inserting a mixture of gases with known concentrations into an optical path of electromagnetic radiation (e.g., using a sealed gas cell, or a "puff" of gas), and comparing the intensities of the received electromagnetic radiation across the electromagnetic wavelength spectrum with expected intensities based on the predetermined concentrations of the gases. If the expected intensities are shifted from the measured intensities along the wavelength spectrum, the wavelength scale may be shifted by an integer amount of pixels to correct for the shift. Such a method for calibrating for "wavelength drift" may be inefficient because the introduction of the mixture of gases of known concentrations into the optical path may require additional system capabilities (e.g., positioning a gas cell, providing a "puff" of gas, etc.). This method may also be inaccurate because it only enables calibration for "wavelength drift" that is at least as large as on pixel of the sensor array. In other words, current solutions for correcting for "wavelength drift" may not enable for corrections of "wavelength drift" smaller than a single pixel.

These and other drawbacks exist with known methods for correcting for "wavelength drift" in RES systems.

SUMMARY

The invention solving these and other problems relates to a RES system and method incorporating spectral matching by data interpolation.

One aspect of the invention relates to a system and method for correcting for "wavelength drift" in an RES system. One advantage provided by the invention includes the ability to correct for offset amounts of "wavelength drift" that are not divisible by an integer number of pixels in an optical detector used in the RES system. For example, such offset amounts may include offset amounts that are smaller than a single pixel, and/or other fractional pixel offset amounts (e.g., 1½ pixels, 2¼ pixels, etc.). Correction of fractional pixel offset amounts may enhance spectral matching, enable substantially continuous calibration of an RES system, and provide other benefits.

According to one implementation, the RES system may comprise at least a radiation source, a detector, and a processor. The source may emit electromagnetic radiation within a predetermined wavelength spectrum along an optical path. The detector may receive the electromagnetic radiation from the source. The source and the detector may be configured such that the electromagnetic radiation passes through an exhaust plume of a passing vehicle as the vehicle travels along a roadway. Upon receiving the electromagnetic radiation, the detector may generate a plurality of output signals, and provide the output signals to the processor. The output signals may be processed to determine the concentrations of the gases in the exhaust plume in a known manner.

According to various embodiments of the invention, the detector may include a spectrometer that spatially arranges the electromagnetic radiation by wavelength, so that the intensity of the electromagnetic radiation within wavelength regions that correspond to absorption bands of one or more gases may be monitored. The spectrometer may include a diffraction element and a sensor comprising an array of sensor pixels. In some embodiments, the diffraction element may spatially separate the electromagnetic radiation based on wavelength. The sensor pixels may be arranged to receive the spatially arranged light such that each sensor pixel may receive a substantially unique wavelength range of electromagnetic radiation.

In some implementations, the sensor pixels may comprise light sensitive elements, such as diodes or other elements, capable of generating output signals proportional to the intensity of the electromagnetic radiation incident thereon. In one implementation wherein the electromagnetic radiation from the optical path is spatially separated into a one-dimensional spectrum, the sensor may comprise a one-dimensional array of sensor pixels (e.g., a 128 diode array) arranged such that the one-dimensional spectrum of electromagnetic radiation may be incident on the sensor during operation of the system. In such an implementation, since the electromagnetic radiation is spatially arranged based on wavelength, the electromagnetic radiation incident on a particular sensor pixel may have a wavelength that falls within a wavelength range unique (or substantially unique) to that sensor pixel. Based on the intensity of the received electromagnetic radiation (e.g., the radiation within the sensor pixel's wavelength range), the sensor pixel may generate an output signal with a signal value (e.g., voltage of the signal, current of the signals, a digital signal value, etc.) proportional to the intensity of the received electromagnetic radiation, thereby enabling the intensity of electromagnetic radiation within the wavelength range of that particular sensor pixel to be monitored. The output signals of the sensor pixels may be output from the detector to the processor for processing.

According to various embodiments of the invention, the processor may execute a software program or application comprising an intensity versus wavelength profile module, a scale module, a storage module, a concentration module, and/or other modules. The intensity versus wavelength profile module may determine an intensity versus wavelength profile of the electromagnetic radiation received by the detector based on the signal values of the received output signals. Since each of the sensor pixels may receive electromagnetic radiation within a substantially unique wavelength range, the magnitudes of the signal values may indicate the intensities of the electromagnetic radiation on the various sensor pixels. From the measurements of intensities of the electromagnetic radiation, the intensity versus wavelength profile of the electromagnetic radiation transmitted along the optical path from the source to the detector may be determined.

In some embodiments, determining an intensity versus wavelength profile for the electromagnetic radiation may include associating spectral data from the output signals of the sensor pixels with the appropriate wavelengths of electromagnetic radiation. This may include associating the intensity versus wavelength profile with wavelengths based on a scale. In some instances, the scale may be stored within the storage module, and may associate the output signals with the wavelengths, or wavelength ranges, of the electromagnetic radiation incident on the corresponding sensor pixels.

According to various embodiments of the invention, the concentration module may determine the concentration of one or more gases in the optical path based on the intensity versus wavelength profile determined by the intensity versus wavelength profile module. For example, a particular gas present in the optical path may absorb electromagnetic radiation within a wavelength absorption band. Since the amount of electromagnetic radiation absorbed is related to the concentration of the gas present in the optical path, the determination of the concentration of the gas by the concentration module may be based on the observed absorption dip of an intensity versus wavelength profile within the wavelength absorption band.

In some embodiments, the scale module may correct the detection of the spectral intensity of electromagnetic radiation within the system by adjusting the scale used to associate the output signals from the sensor pixels with the appropriate wavelengths. The scale module may adjust the scale to account for offset amounts of "wavelength shift" that are not divisible by an integer number of pixels (e.g., fractional pixel offset amounts). The adjustment of the scale may be performed by the scale module based on the output signals of the sensor pixels while the exhaust plume of the vehicle is present in the optical path.

Another aspect of the invention relates to a method of adjusting the scale based on signal values of output signals from the sensor pixels. In some implementations, the method may be performed by the scale module. The method may include triggering the adjustment of the scale. The trigger may comprise a detection of the exhaust plume in the optical path. In some instances, adjustment of the scale may be triggered with each vehicle pass. Other triggering mechanisms may be utilized. Once the method has been triggered, spectral data may be received by the scale module. The spectral data may be derived from the output signals generated by the sensor pixels while the exhaust plume is in the optical path. The received spectral data may be compared by the scale module with predetermined reference spectral data to determine an offset amount of "wavelength drift" in the detector. The comparison between the reference spectral data and the received spectral data may include a peak-matching algorithm. The scale module may then complete the calibration by adjusting the scale to account for the offset amount of "wavelength drift" determined in the comparison between the reference spectral data and the received spectral data.

These and other objects, features, benefits, and advantages of the invention will be apparent through the detailed description of the preferred embodiments and the drawings attached hereto. It is also to be understood that both the foregoing general description and the following detailed description are exemplary and not restrictive of the scope of the invention.

DETAILED DESCRIPTION

Prior to describing the RES system and method incorporating spectral matching by data interpolation, a description of an exemplary RES system for remotely monitoring the exhaust gas composition of motor vehicles on a roadway or driving surface at a given test site (or in the "field") under various operating conditions will first be provided. The calibration/correction methods disclosed herein can be used with this or other system configurations. Embodiments of the invention may include all or some of the RES system components as described below, or other components.

Figure 1:
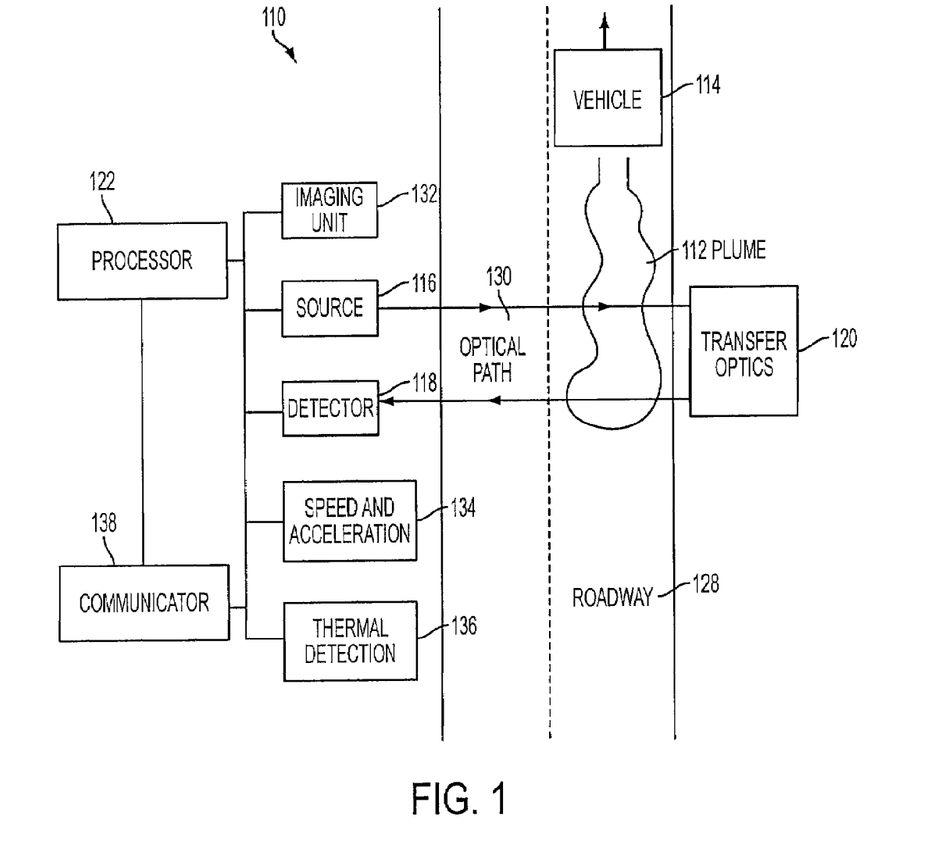
FIG. 1 is an exemplary illustration of a system for remotely sensing the concentration of one or more gases in an exhaust plume emitted by a vehicle, according to an embodiment of the invention.

FIG. 1 illustrates a RES system 110 according to one or more implementations of the invention. RES system 110 measures emissions in an exhaust plume 112 (from a motor vehicle 114) in an optical (or measurement) path 130 on a roadway 128. Roadway 128 may comprise a single or multi-lane roadway, or any other roadway or driving surface suitable for the safe passage of vehicle 114 under various operating conditions. Alternatively, roadway 128 may comprise a test lane designated for vehicle emissions testing, wherein vehicle 114 may be tested under a variety of operating conditions. RES system 110 may comprise a source 116, a detector 118, a processor 122, and/or other components.

As previously recited, source 116 may comprise one or more sources of electromagnetic radiation (ER) and detector 118 is preferably chosen to permit detection of electromagnetic radiation emitted by source 116. Source 116 may be selected to provide electromagnetic radiation with spectral characteristics that facilitate the detection of one or more predetermined gases present in exhaust plume 112. For example, nitric oxide, ammonia, and sulfur dioxide may be measured using UV electromagnetic radiation. Nitrogen dioxide, for example, may be measured using electromagnetic radiation with a wavelength of 430 nm.

According to one embodiment, the RES system 110 may comprise transfer optics 120 configured to allow radiation from source 116 to be directed to detector 118 for analysis. Transfer optics 120 may comprise a mirror, flat mirror, lateral transfer mirror (LTM), vertical transfer mirror (VIM), retroflector, or other device. In one embodiment, transfer optics 120 may comprise a lateral transfer mirror to reflect radiation from source 116 along a path displaced laterally or vertically, depending on orientation, from the incident direction. Other configurations may be used.

Processor 122, as will be described further below, may employ software to accomplish desired analysis of collected and/or stored data, and to carry-out one or more of the calculations described in the calibration methods set forth herein.

With regard to an exhaust gas sample present in optical path 130, software may be used to calculate the relative amounts of various exhaust gas constituents, concentrations of various exhaust gas constituents (e.g., HC, $CO_2$, $NO_x$, CO, etc.), the decay rate (e.g., dissipation in time) of the exhaust constituents, and the opacity of the exhaust plume.

According to an embodiment of the invention, processor 122 may calculate the relative amounts of various exhaust gas constituents in exhaust plume 112 of vehicle 114 (as vehicle 114 passes by (or through) the RES system 110) by computing the ratio of the absorption for a particular exhaust gas constituent to the $CO_2$ absorptions, in a known manner. This eliminates the need to calculate the total amount of exhaust plume present since the calculated ratios may provide sufficient information to identify vehicles which do or do not meet predetermined pollution criteria.

Processor 122 may further comprise software to accomplish other data analysis functions. For example, vehicle emission data may be checked for running losses. Running losses may typically include emission readings due to fuel system leaks on a vehicle (e.g., leaky fuel tank filler cap, fuel line, etc.), blow-by emissions (e.g., crank case emissions blowing by the piston rings), emissions due to other vehicles in the vicinity, or other systematic losses.

Processor 122 may also include software to accomplish various vehicle owner notification functions. For example, the owner of a vehicle that has been recorded as being in compliance with certain predetermined emission levels may receive a notification. Coordination with local authorities may be arranged to grant vehicle owners a waiver or pass of local emission certification procedures upon receiving such a notification. Likewise, vehicles that fail to meet predetermined emission levels may receive a notification requiring the owner to remedy the non-compliance. Other data processing functions are also possible. Processor 122 may also interface to, control, and/or collect and reduce data from an imaging unit 132, a speed and acceleration detection unit 134, and thermal detection unit 136.

In various embodiments, RES system 110 may comprise an imaging unit 132 to capture and/or record an image of vehicle 114 passing by (or through) the RES system 110 in a known manner. Imaging unit 132 may be positioned to record an image of vehicle 114 at any predetermined number of locations. Imaging unit 132 may comprise, for example, a film camera, video camera, or digital camera. Other imaging devices may also be used.

Preferably, imaging unit 132 may record an image of the identification tag (e.g., license plate) of vehicle 114. Tag information may be processed by processor 122 to provide additional information about the vehicle. For example, Motor Vehicle Department databases may be accessed to retrieve owner information, make, model type, model year, or other information. In some embodiments, this additional information may be incorporated into the emission sensing data analysis. For example, the make and model year of the vehicle may be used to determine input information for certain processing steps, including information such as whether the vehicle includes a carburetor or fuel injector, whether the car runs on diesel fuel or gasoline, etc.

According to an embodiment of the invention, the RES system 110 may include a speed and acceleration detection unit 134. Preferably, the speed and/or acceleration of vehicle 114 may be measured as it passes through the RES system 110 using speed and acceleration detection unit 134 in a known manner.

In one embodiment, speed and acceleration detection unit 134 may comprise an arrangement of laser beams or other light beams associated with timing circuitry. The laser or light beams may be arranged to traverse the path of vehicle 114 at various points. As vehicle 114 passes, it will cause interruptions in the laser or light beams. The times at which the beam interrupts occur may be used to calculate the vehicle's speed and/or acceleration. Other methods of determining vehicle speed and/or acceleration may also be used or incorporated into the RES system 110.

Alternatively, the laser or light beams or radar beams may be arranged to intercept the path of vehicle 114 as it drives along roadway 128. For example, radar systems may be used to determine vehicle speed and acceleration. Alternatively, transducers, piezoelectric elements, or other "drive over" detectors may be placed at locations in the roadway to monitor vehicle passage. Preferably, speed and/or acceleration data may be input into processor 122 to help characterize vehicle operating conditions (e.g., accelerating or decelerating), or to determine which vehicle is to be associated with a particular sensor measurement. Other configurations and uses of speed and acceleration data are also possible.

Some embodiments of the invention may incorporate a thermal detection unit 136. Preferably, thermal detection unit 136 may comprise a non-contact thermometer system. For example, an IR thermometer may be used to optically detect the temperature of remote objects. Other temperature detection systems may also be used. Thermal detection unit 136 may, for example, be used to detect the temperature of portions of the vehicle passing through the RES system 110. Some embodiments may use direct sensing of the area of interest. For example, an IR thermometer may be aimed at the underside of a passing vehicle to detect the temperature(s) of vehicle components (e.g., engine, catalytic converter, muffler, etc.). Indirect sensing may also be used. For example, an IR thermometer may be aimed at the roadway to measure the heat of the passing vehicle which is reflected from the roadway surface.

Thermal information that is detected by thermal detection unit 136 may be used to indicate that an engine has just recently been started (e.g., the engine is "cold" or has not reached normal operating temperature). Such a cold engine reading may be used, for example, to initiate an alternative data processing routine. Certain embodiments of the invention may reduce the chance of a potentially misleading reading by also detecting the temperature of other portions of the vehicle. Other uses for collected thermal data are also possible. Thermal detection of the exhaust plume of a vehicle and/or ambient temperatures may also be used in connection with various aspects of the invention.

According to one embodiment of the invention, an identification tag on vehicle 114 may be read to identify the vehicle and associate particular sensed vehicle emission information with the vehicle. An identification tag, defined as a license plate above, may also comprise a transponder located on or within vehicle 114 (e.g., hung from a rear view mirror, placed on the dashboard, etc.), or that is integral within the vehicle (e.g., part of a global positioning system ("GPS"), located within the engine of the vehicle, or placed or mounted elsewhere). The transponder may transmit information about vehicle 114, including make and model of vehicle 114, engine characteristics, fuel type, the owner of vehicle 114, or other information which may be pertinent. According to an embodiment of the invention, a transponder may be used in connection with other functions. For instance, a transponder may also be used in connection with a toll pass, whereby a driver can electronically pay tolls via the transponder without stopping the vehicle.

An identification tag may also comprise a tag or decal that requires a reader. By way of example, an identification tag may comprise a decal with identifying marks (e.g., bar codes, infrared markings, etc.) containing information about vehicle 114. The decal may be located outside vehicle 114, such as on a front or rear bumper, on the under-side of vehicle 114, or any other location on vehicle 114 where the decal may be suitably read. A reader may observe the decal and thereby obtain information about vehicle 114. One embodiment employs a bar code placed on the roof of vehicle 114, which can be read by a reader placed above vehicle 114.

A receiver may be used to obtain information from an identification tag. According to an embodiment of the invention, an antenna may receive signals transmitted from an identification tag containing a transponder. Any type of conventional receiver may be used to receive signals. According to an embodiment of the invention, one reader and/or receiver may be used in connection with multiple lanes. Based on the signal received or the decal read, a receiver or reader may determine in which lane a particular vehicle is located at a particular time.

According to an embodiment of the invention, processor 122 may receive vehicle information. Processor 122 may receive information about vehicle 114 from a reader and/or receiver. Vehicle information and information obtained by sensing vehicle emissions may be stored. Processor 122 may correlate vehicle information received from an identification tag with the results from vehicle emissions sensing. Processor 122 may update a vehicle record to account for the results obtained by processing vehicle emission data, such as information regarding whether a vehicle has passed or failed predetermined emissions criteria.

According to an embodiment of the invention, RES system 110 may further comprise a communicator 138. Communicator 138 may communicate information such as, for example, measured vehicle emissions and identification tag information from RES system 110 to various other locations (e.g., Motor Vehicle Departments, a central data repository, servers, etc.) for storage, processing, viewing, or other use in a known manner. Communicator 138 may transmit and/or receive information via a wire connection, such as cable or telephone line, or a wireless connection, such as by a radio, cellular, or satellite transmitter, or via any other type of suitable wireless communication.

In some embodiments, communicator 138 may comprise appropriate hardware and/or software to enable processor 122 to be accessed remotely over a network (not illustrated) via a communications link (not illustrated). The network may include any one or more of, for instance, the Internet, an intranet, a PAN (Personal Area Network), a LAN (Local Area Network), a WAN (Wide Area Network), a SAN (Storage Area Network), or a MAN (Metropolitan Area Network). The communications link may include any one or more of, for instance, a telephone line, a Digital Subscriber Line (DSL) connection, a Digital Data Service (DDS) connection, an Ethernet connection, an Integrated Services Digital Network (ISDN) line, an analog modem connection, a cable modem connection, or a wireless connection. In this regard, a user (e.g., an emissions test administrator or other individual) at a remote computer terminal can administer emissions tests, and/or analyze or process data. Thus, RES system 110 may, in various embodiments, comprise either manned or unmanned systems.

As recited above, alternative RES system 110 configurations may exist incorporating some or all of the aforementioned system components. Accordingly, RES system 110 (as illustrated in FIG. 1) should not be viewed as limiting.

As an example, in certain embodiments (not illustrated), source 116 and detector 118 may be placed on opposite sides of roadway 128. Various components of speed and acceleration detection unit 134 and thermal detection unit 136 may also be positioned on opposite sides of roadway 128.

In another embodiment (not illustrated), RES system 110 may comprise a compact, unmanned system that may be used for unattended monitoring of vehicle emissions data (also referred to as a "bunkered" unit). In such an embodiment, source 116, detector 118, imaging unit 132, processor 122, communicator 138, and various components of speed and acceleration detection unit 134 and thermal detection unit 136 may be housed together on a first side of roadway 128, while transfer optics 120 and various other components of speed and acceleration detection unit 134 and thermal detection unit 136 may be housed together on the opposite side of roadway 128. Other configurations are possible.

Having provided an overview of an exemplary RES system, the RES system and method incorporating spectral matching through data interpolation will now be described.

Figure 2:
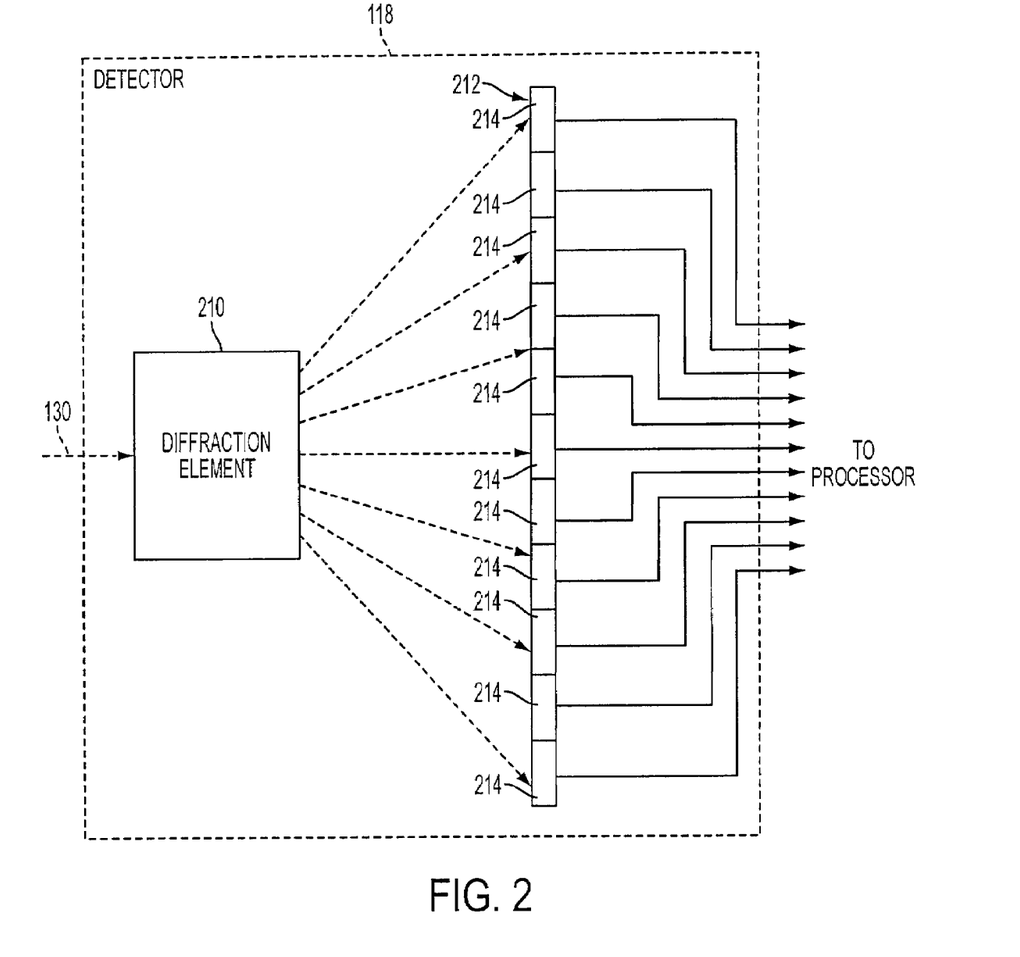
FIG. 2 is an illustration of a detector, according to an embodiment of the invention.

According to one implementation, as shown in FIG. 2, detector 118 may comprise a spectrometer that spatially arranges the electromagnetic radiation by wavelength so that the intensity of the electromagnetic radiation within wavelength regions that correspond to absorption bands of one or more gases may be monitored. Detector 118 may comprise a spectrometer which may include a diffraction element 210, and a sensor 212 made up of an array of sensor pixels 214. Diffraction element 210 may spatially separate the electromagnetic radiation based on wavelength, and sensor pixels 214 may be arranged such that various wavelength ranges of the electromagnetic radiation are incident thereon.

In one implementation, diffraction element 210 may comprise a transmissive element such as a prism, a transmissive diffraction grating, or other transmissive optical elements capable of diffracting electromagnetic radiation. In an alternative implementation, diffraction element 210 may comprise a reflective element such as a reflective diffraction grating or other reflective optical elements capable of reflecting and separating electromagnetic radiation by wavelength. Diffraction element 210 may comprise a holographic diffraction element, or another type of diffraction element. In one implementation, diffraction element 210 may spatially separate the electromagnetic radiation from optical path 130 into a one-dimensional spectrum based on wavelength.

According to one aspect of the invention, sensor pixels 214 included in sensor 212 may include light sensitive elements, such as diodes or other elements, capable of generating output signals proportional to the intensity of the electromagnetic radiation incident thereon. In one implementation in which the electromagnetic radiation from optical path 130 (FIG. 1) may be spatially separated into a one-dimensional spectrum, sensor 212 may include a one-dimensional array of sensor pixels 214 (e.g., a 128 diode array) arranged such that the one-dimensional spectrum of electromagnetic radiation may be incident on sensor 212 during operation of system 110. In such an implementation, since the electromagnetic radiation is spatially arranged based on wavelength, the electromagnetic radiation incident on a particular sensor pixel 214 may have a wavelength that falls within a wavelength range unique (or substantially unique) to that sensor pixel 214. Based on the intensity of the received electromagnetic radiation (e.g., the radiation within the sensor pixel 214's wavelength range), sensor pixel 214 may generate an output signal with a signal value (e.g., voltage of the signal, current of the signals, a digital signal value, etc.) proportional to the intensity of the received electromagnetic radiation, thereby enabling the intensity of electromagnetic radiation within the wavelength range of that particular sensor pixel 214 to be monitored. The output signals of sensor pixels 214 may be output from detector 118 to processor 122 for processing.

Figure 3:
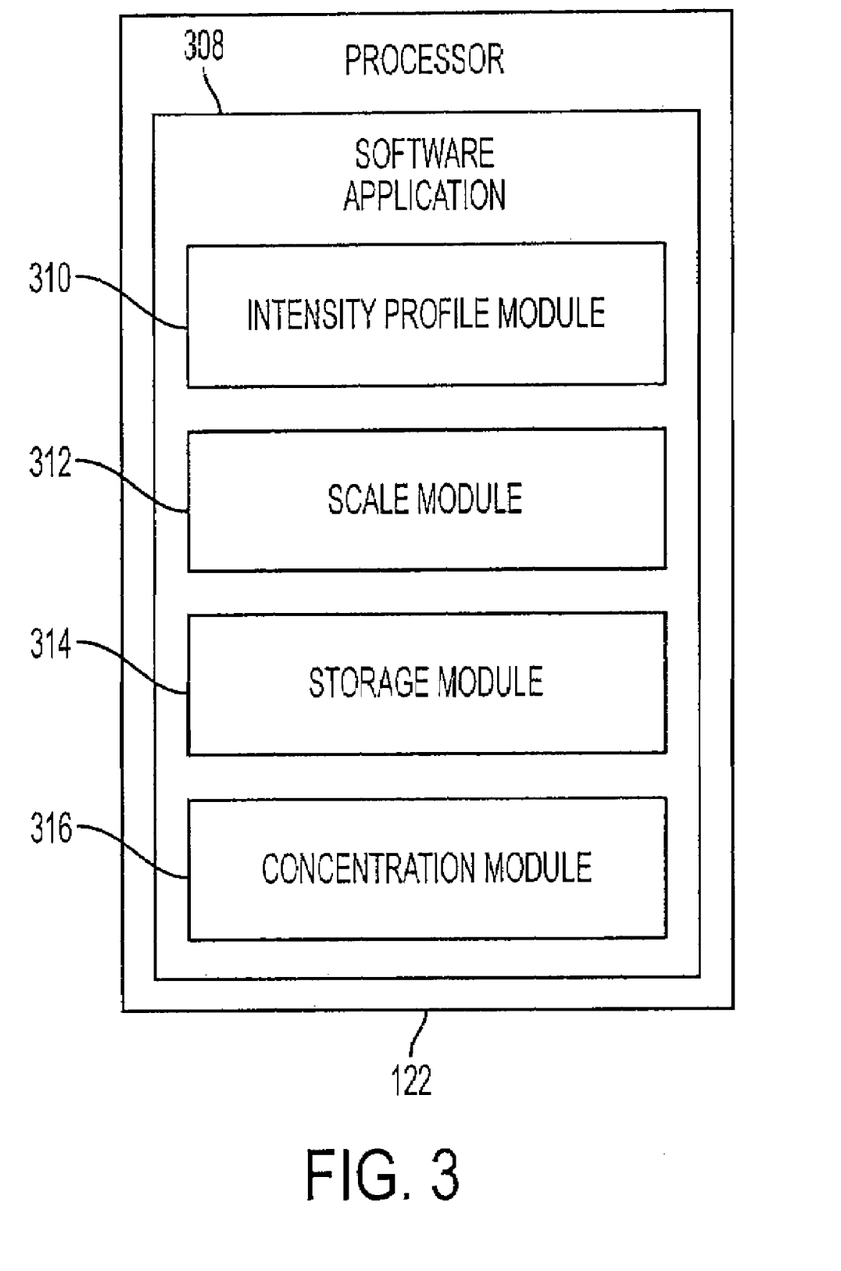
FIG. 3 is an illustration of a processor, according to an embodiment of the invention.

Referring to now FIG. 3, processor 122 may execute a software application 308 comprising an intensity versus wavelength profile module 310, a storage module 312, a scale module 314, a concentration module 316 and/or other modules. It should be understood that while processor 122 is shown in FIG. 3 (and FIG. 1) as a single entity, these depictions are provided merely for illustrative purposes. Processor 122 may comprise more than a single processing entity (e.g., a single processor chip or circuit). For example, processor 122 may include a plurality of actual processing units, electronic storage units, and/or other system components. Additionally, in some instances, one or more of modules 310, 312, 314, and/or 316 of application 308 may be executed by processor 122 remotely from others of modules 310, 312, 314, and/or 316. Those having skill in the art will also appreciate that in some implementations, each of modules 310, 312, 314, and 316 may be implemented in hardware, software, firmware, or some combination thereof.

Figure 4:
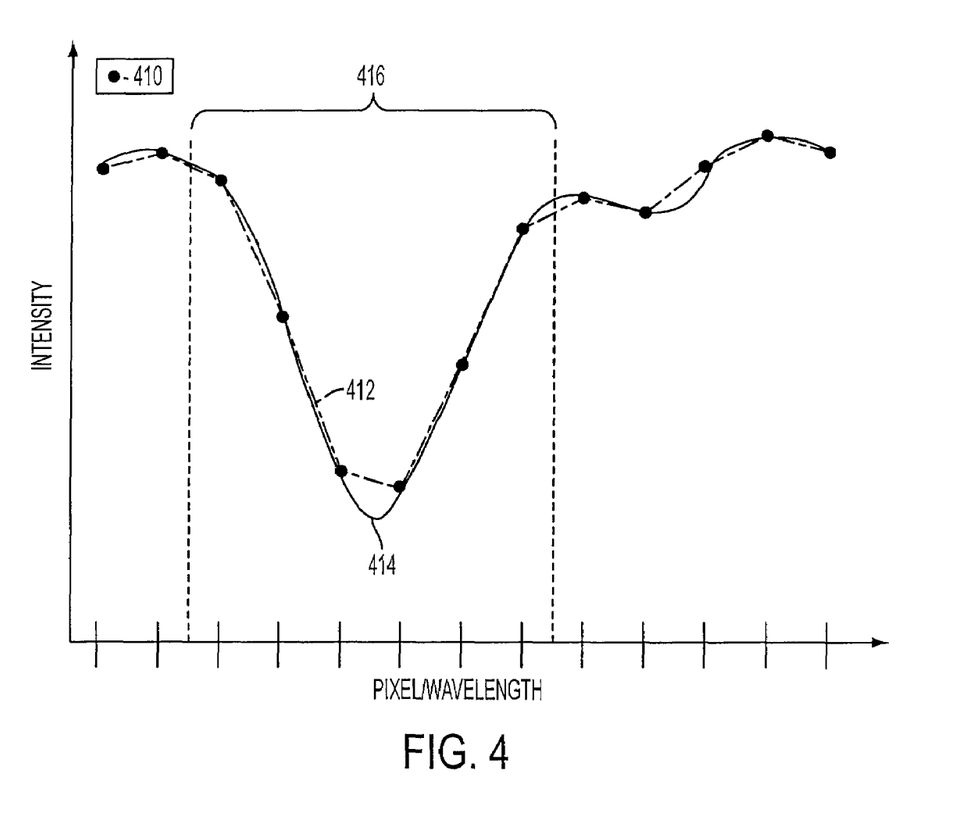
FIG. 4 is an illustration of one or more intensity versus wavelength profiles, according to an embodiment of the invention.

According to one aspect of the invention, output signals from sensor pixels (e.g., sensor pixels 214 of FIG. 2) may be provided to processor 122. Intensity versus wavelength profile module 310 may generate an intensity versus wavelength profile of the electromagnetic radiation received by detector 118 based on the signal values of the received output signals. FIG. 4 is an exemplary illustration of an intensity versus wavelength profile that may be generated by intensity versus wavelength profile module 310. The graphic illustration includes a plurality of sensor pixel data points 410 that correspond to sensor pixels 214 (FIG. 2), plotted as a function of the signal value of the output signals of sensor pixels 214. As previously recited, each of sensor pixels 214 may receive electromagnetic radiation within a substantially unique wavelength range, and the magnitudes of the signal values may indicate the intensities of the electromagnetic radiation on the various sensor pixels 214. Therefore, each sensor pixel data point 410 may represent (e.g., be proportional to) an intensity of the electromagnetic radiation transmitted along optical path 130 (from source 116 to detector 118) within the wavelength range that corresponds to the one of sensor pixels 214 associated with that particular sensor pixel data point 410. From these measurements, an intensity versus wavelength profile of the electromagnetic radiation may be generated by interpolating spectral data between sensor pixel data points 410, and associating the spectral data (both the interpolated spectral data and the spectral data of sensor pixel data points 410) with the appropriate electromagnetic wavelengths.

For instance, as depicted in FIG. 4, sensor pixel data points 410 may be arranged such that sensor pixel data points 410 that correspond to successive wavelength ranges may be ordered consecutively. Intensity versus wavelength profile module 310 may implement one of a variety of methods for interpolating spectral data between sensor pixel data points 410. For example, spectral data (illustrated as plot 412) may be interpolated from sensor pixel data points 410 by expressing intensities between sensor pixel data points 410 as a first-order polynomial (e.g., a straight line). Alternatively, spectral data 414 may be interpolated from sensor pixel data points 410 by expressing spectral data between sensor pixel data points 410 as a higher order polynomial (e.g., a third-order polynomial) to smooth the overall shape of the interpolated spectral data 414.

In one implementation, determining an intensity versus wavelength profile for electromagnetic radiation received by detector 118 may include associating the spectral data included in the intensity versus wavelength profile with the appropriate wavelengths of electromagnetic radiation. This may include associating the intensity versus wavelength profile with wavelengths based on a scale. In some instances, the scale may be determined and/or adjusted by scale module 312, and/or stored within storage module 314. The scale may associate sensor pixel data points 410 with appropriate wavelengths, or wavelength ranges, thereby enabling the spectral data interpolated between sensor pixel data points 410 to be associated with appropriate wavelengths. The wavelengths, or wavelength ranges, associated with sensor pixel data points 410 by the scale may substantially coincide with the wavelength ranges of the electromagnetic radiation incident on the separate sensor pixels 214 within detector 118 that correspond to sensor pixel data points 410.

Once intensity versus wavelength profile module 310 has generated an intensity versus wavelength profile by interpolating spectral data between sensor pixel data points 410, and associating the spectral data with the appropriate wavelengths, the intensity versus wavelength profile may represent the intensity of the electromagnetic radiation in terms of wavelength. With respect to FIG. 4, this may be represented by equating the horizontal axis with the wavelength of the electromagnetic radiation received by detector 118, and equating the vertical axis with the intensity of the received electromagnetic radiation.

According to one implementation, concentration module 316 may determine the concentration of one or more gases in optical path 130 based on the intensity versus wavelength profile generated by intensity versus wavelength profile module 310. For example, a particular gas present in optical path 130 may absorb electromagnetic radiation within a wavelength absorption band 416 as shown in FIG. 4. Since the amount of electromagnetic radiation within wavelength absorption band 416 absorbed may be related to the concentration of the gas present in optical path 130, the determination of the concentration of the gas by concentration module 316 may be based on the observed absorption dip of an intensity versus wavelength profile (e.g., intensity versus wavelength profile 412 or intensity versus wavelength profile 414) within wavelength absorption band 416.

Over time, as the spatially arranged electromagnetic radiation incident on sensor 212 within detector 118 wanders, causing "wavelength drift" in detector 118, the scale used by intensity versus wavelength profile module 310 to associate the spectral data with the appropriate wavelengths may become inaccurate. For example, "wavelength drift" in detector 118 may cause the intensity versus wavelength profile to be "shifted" such that the wavelengths, or wavelength ranges, associated with the spectral data of the intensity versus wavelength profile are offset by an offset amount. A shift in the intensity versus wavelength profile may result in inaccuracies by concentration module 316 in determining the concentrations of the gases using the intensity versus wavelength profile.

To account for these and other inaccuracies due to "wavelength drift," scale module 312 may calibrate for "wavelength drift" in the detection of spectral intensity of electromagnetic radiation within RES system 110. For example, correcting for "wavelength drift" may include determining a scale, shifting a scale, and/or taking other actions to enhance the accuracy of the scale used by intensity versus wavelength profile module 310 in associating spectral data with appropriate wavelengths, or wavelength ranges.

According to one aspect of the invention, scale module 312 may adjust the scale to correct for a "fractional pixel shift" in the intensity versus wavelength profile due to "wavelength drift." A "fractional pixel shift" may include a shift in the wavelengths of the intensity versus wavelength profile that is not divisible by an integer number of wavelength ranges over which the electromagnetic radiation is received at sensor pixels 214. In some implementations, scale module 312 may adjust the scale based on signal values of the output signals from sensor pixels 214 while exhaust plume 112 of vehicle 114 is present in optical path 130.

Figure 5:
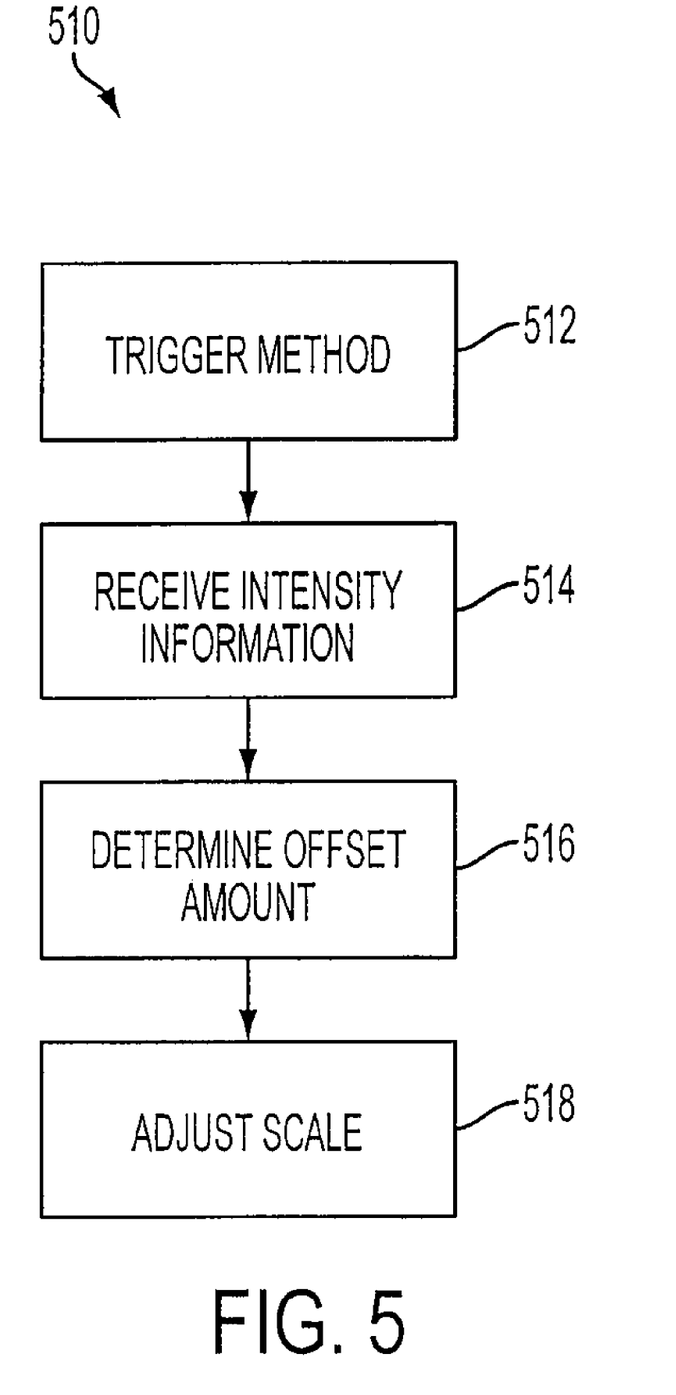
FIG. 5 depicts a flowchart of processing information, according to an embodiment of the invention.

FIG. 5 illustrates a method 510 of adjusting a scale based on signal values of output signals from sensor pixels 214. The various operations of method 510 may be executed by the components of RES system 110. For example, scale module 312 may execute method 510. However, it should be appreciated that method 510 may be implemented by other systems and/or components other than those shown in the drawings.

In an operation 512, method 510 may be triggered. In some instances, the triggering of method 510 may be based on a determination of a presence of exhaust plume 112, or another mixture of gases that includes one or more gases to be monitored, in optical path 130. Method 510 may also be triggered based on a detection of vehicle 114 by component 124. For example, in one implementation, component 124 may comprise an imaging device (e.g., a video imaging device, a still imaging device, etc.) and method 510 may be triggered based on an image of vehicle 114 captured by component 124. In another example, component 124 may include an optical trigger that emits a beam of electromagnetic radiation across road 128 and detects the presence of vehicle 114 based on the beam becoming blocked. Other implementations in which method 510 may be triggered based on a detection of vehicle 114 by component 124 exist.

In some implementations, method 510 may be triggered based on the output signals generated by sensor pixels 214. For instance, method 510 may be triggered based on the signal values of the output signals indicating that optical path 130 is blocked (e.g., by vehicle 114). In other instances, method 510 may be triggered based on a determination by concentration module 316, based on the output signals, that a concentration of a gas is greater than a concentration threshold. For example, the concentration may include a predetermined optical depth. In one non-limiting embodiment, the concentration threshold may include an optical depth of nitric oxide of 8,000 ppm*cm.

Other implementations for triggering method 510 (based on determination of a presence of exhaust plume 112 or of another mixture of gases in optical path 130) may be implemented at operation 512. In some implementations, for example, method 510 may be triggered for each vehicle passing through optical path 130. This may provide for substantially continuous calibration for "wavelength drift" to system 110. In other implementations, method 510 may not be triggered at each vehicle pass.

In an operation 514, spectral data corresponding to the signal values generated by detector 118 may be received. In some implementations, the spectral data may be received by scale module 316 from intensity versus wavelength profile module 310. For example, the spectral data may include a set of sensor pixel data points derived from output signals generated by detector 118.

In an operation 516 an amount of "wavelength drift" present within detector 118 may be determined based on the received spectral data. The amount of "wavelength drift" may be quantified as an offset amount, as recited above. In some implementations, a peak-matching algorithm may be applied to the received spectral data to determine the offset amount.

Figure 6:
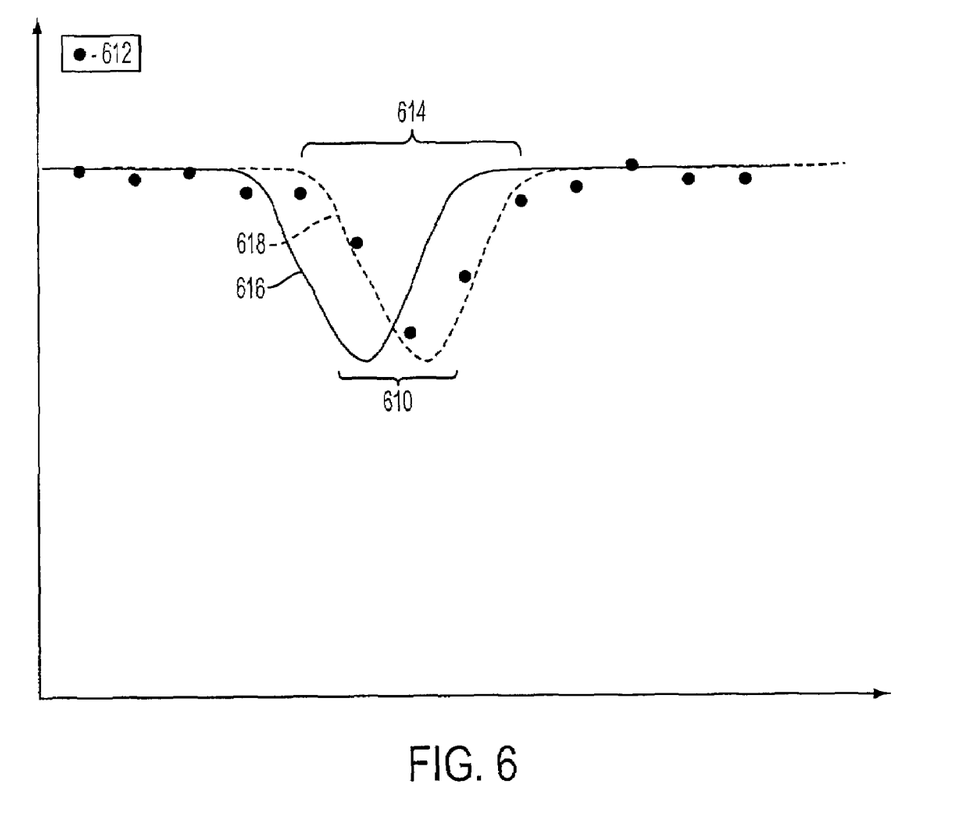
FIG. 6 is an illustration of a comparison of spectral data, according to an embodiment of the invention.

FIG. 6 illustrates one such implementation in which the peak-matching algorithm may align reference spectral data 610 with received spectral data 612 (e.g., a set of sensor pixel data points). Reference spectral data 610 may have a shape that corresponds to a predicted shape of an absorption dip 614 in received spectral data 612 In some implementations, reference spectral data 610 may be determined using a predetermined reference intensity function, such as a spline function (e.g., a cubic spline), or other functions. In order to align reference spectral data 610 with received spectral data 612, reference spectral data 610 may be shifted from an initial alignment 616 to a modified alignment 618.

Initial alignment 616 of reference spectral data 610a may be based on the scale currently in use (or in use just prior to the triggering of method 510) by intensity versus wavelength profile module 310. In other words, initial alignment may be based on a predicted shape and spectral location of received spectral data 612, as determined according to the current scale.

At modified alignment 618, one or more peaks in reference spectral data 610 may be aligned with one or more corresponding peaks in received spectral data 612. Based on the shift applied to reference spectral data 610 from initial alignment 616 to modified alignment 618, the offset amount of "wavelength drift" in detector 118 may be determined. For example, the shift applied to reference spectral data 610 may be related to (e.g., substantially proportional or equal to) the offset amount of "wavelength drift" in detector 118.

Figure 7A:
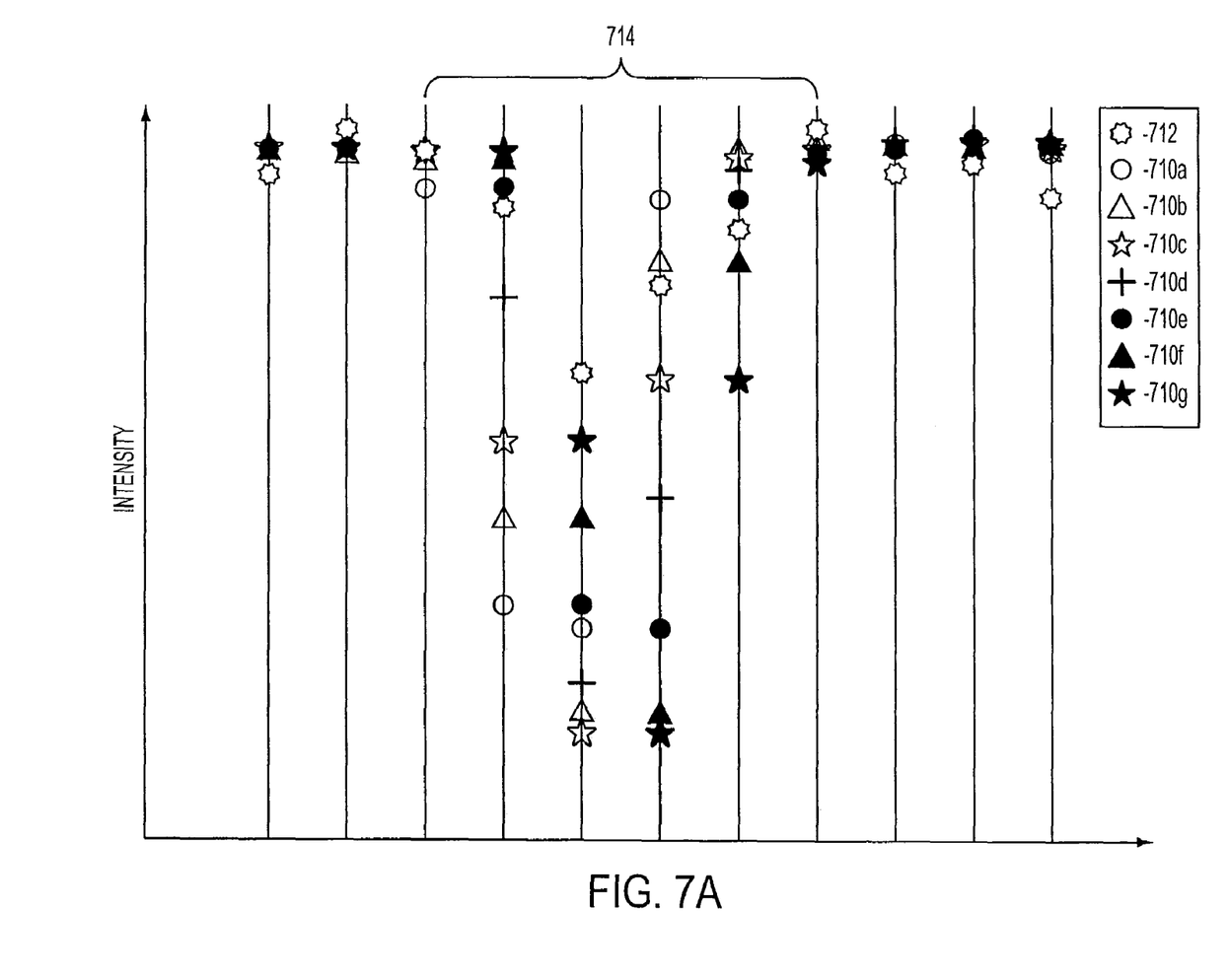
FIGS. 7A-7B are illustrations of a comparison of spectral data, according to one embodiment of the invention.

FIG. 7A illustrates another implementation in which a peak-matching algorithm may be applied to the received spectral data to determine the offset amount of "wavelength drift" in detector 118. As illustrated, a plurality of predetermined sets of reference spectral data may be compared with the received spectral data. The sets of reference spectral data may include sets of references pixel data points 710a-710g, which may be compared with a received set of sensor pixel data points 712. Sets of reference pixel data points 710a-710g may correspond to a predicted shape of an absorption dip 714 in sensor pixel data points 712, due to the presence of a gas in optical path 130.

Sets of reference pixel data points 710a-710g may comprise a base set of reference pixel data points 710d. Base set of reference pixel data points 710d may be a prediction of sensor pixel data points 712 based on the scale currently in use (or the scale in use just prior to the triggering of method 510) by intensity versus wavelength profile module 310 to associate sensor pixel data points 712 with appropriate wavelength ranges.

Sets of reference pixel data points 710a-710g may comprise a plurality of offset sets of reference pixel data points 710a-710c and 710e-710g. Offset sets of reference pixel data points 710a-710c and 710e-710g may be predictions of sensor pixel data points 712 shifted from base set of reference pixel data points 710d to account for "wavelength drift" of various offset amounts. For instance, each of offset sets of reference pixel data points 710a-710c and 710e-710g may be a prediction of sensor pixel data points 712 shifted from base set of reference pixel data points 710d to account for "wavelength drift" of fractional pixel offset amounts. For example, in the implementation illustrated in FIG. 7A, the offset amounts may include ascending and descending increments of ¼ of the size of the wavelength ranges associated with each of sensor pixel data points 712 (e.g., ¼ pixel increments).

Figure 7B:
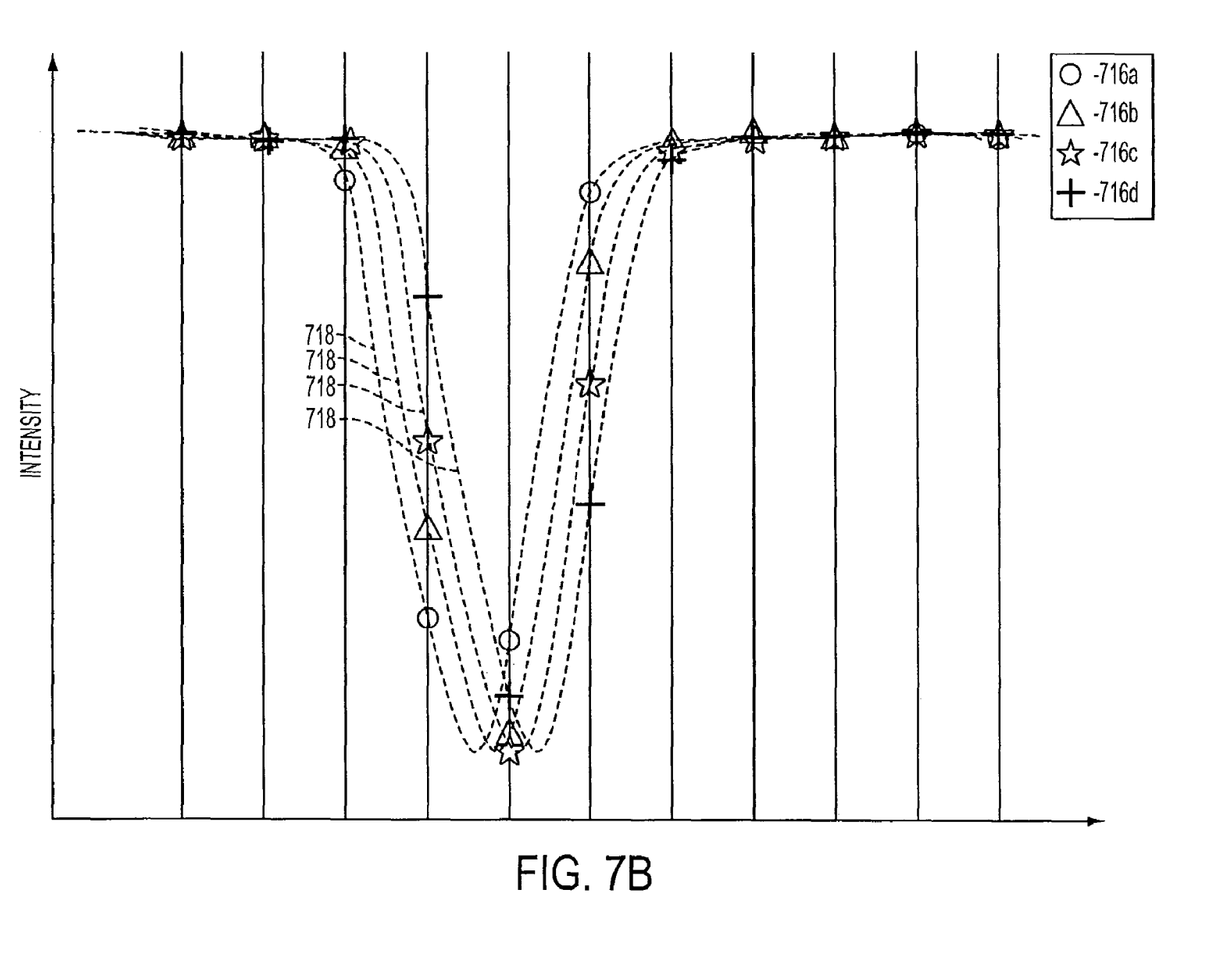

In some implementations, sets of reference pixel data points 710a-710g may be derived from stored sets of data points, wherein the stored sets of data points may be shifted from each other to account for predetermined, incremental, fractional pixel offset amounts. For example, FIG. 7B illustrates stored sets of data points 716a-716d determined by shifting a reference function 718 by the predetermined fractional pixel increment (e.g., ¼ pixel) so that stored sets of data points 716a-716d account for offset amounts of "wavelength drift" that span a pixel. In some instances, stored sets of data points 716a-716d may be predetermined from reference function 718 and stored, for example, at storage module 314. Reference function 718 may be designed to describe a predicted shape of an absorption dip reflected in a set of sensor pixel data points (e.g., set of sensor pixel data points 712) due to the presence of the corresponding gas in optical path 130. In order to facilitate the shifting of reference function 718 by the predetermined fractional increment, reference function 718 may be described mathematically as a spline function, such as a cubic spline function, or other mathematical functions.

Referring back to FIG. 7A, according to various implementations of the invention, base set of reference pixel data points 710d may correspond to one of stored sets of data points 716a-716d that optimize the fit between spectrum data and base set of reference pixel data points 710d. For example, base set of reference pixel data points 710d may correspond to stored set of data points 716d. Offset sets of reference pixel data points 710a-710c and 710e-710g may include a first group of offset sets of reference data points 710a-710c and a second group of offset sets of reference pixel data points 710e-710g. The first group of offset sets of reference pixel data points 710a-710c may correspond to the other stored sets of data points, specifically, stored sets of data points 716a-716c, respectively. The second group of offset sets of reference pixel data points 710e-710g may also correspond to stored sets of data points 716a-716c, respectively, but may be offset from the first group of sets of reference pixel data points 710a-710c by a full pixel. By providing a first group and a second group of sets of reference pixel data points 710a-c and 710e-g from stored sets of data points 710a-710c, scale module 316 enables detection of an amount of "wavelength shift" present in detector 118 in either direction, at predetermined fractional pixel increments.

In some implementations, comparing sets of reference pixel data points 710a-710g with sensor pixel data points 712 may include performing a peak-match between sets of reference pixel data points 710a-710g and sensor pixel data points 712 to determine a closest match between sets of reference pixel data points 710a-710g. For example, a correlation may be performed between sensor pixel data points 712 and each of sets of reference pixel data points 710a-710g to determine the closest match among sets of reference pixel data points 710a-710g to sensor pixel data points 712.

In some implementations, the correlation may include using a correlation coefficient, a correlation ratio, a correlation matrix, or other correlation metrics to quantify the "closeness" of the relationship between sensor pixel data points 712 and each of sets of reference pixel data points 710a-710g. By quantifying the "closeness" between sensor pixel data points 712 and sets of reference pixel data points 710a-710g, the closest set of reference pixel data points to sensor pixel data points 712 may be determined. Based on the offset amount of "wavelength drift" the closest match among sets of reference pixel data points 710a-710g accounts for, scale module 316 may determine the offset amount of "wavelength drift" in detector 118 (e.g., 0 for base set of reference pixel data points 710d, +¼ pixel for set of reference pixel data points 710e, -¼ pixel for set of reference pixel data points 710b, etc.).

Returning to FIG. 5, once the amount of "wavelength drift" present in detector 118 has been determined (in operation 516), the scale currently in use by intensity versus wavelength profile module 310 may be adjusted to account for the "wavelength drift" in detector 118 in an operation 518. Adjusting the scale may include shifting the scale by the offset amount of the "wavelength" drift determined in operation 516. The adjusted scale may then be stored (e.g., at storage module 314) and/or used by intensity versus wavelength profile module 310 to determine one or more intensity versus wavelength profiles from a set of sensor pixel data points (e.g., sensor pixel data points 712) generated by detector 118. This intensity versus wavelength profile(s) may then be implemented by concentration module 316 to determine concentrations of one or more gases present at optical path 130 that account for the "wavelength drift" present in detector 118, even instances in which the offset amount of "wavelength drift" present in detector 118 may be less than a wavelength range associated with a sensor pixel within detector 118 (e.g., a fractional pixel amount).

It should be understood that although various figures provided in the drawings of this disclosure illustrate mathematical operations performed on test and reference data using graphical plots (e.g., FIGS. 4, 6, and 7), these illustrations are provided for explicatory purposes only, and are intended to describe multiple implementations in which mathematical manipulations to test and reference data may be performed without graphical representation of the information.

The aspect of the invention related to calibrating the detection of spectral intensities of electromagnetic radiation for "wavelength drift" has been described above with respect to a remote emissions system for measuring gas concentrations in exhaust plumes of vehicle. However, it should be appreciated that this aspect of the invention may be extended to other systems that may experience "wavelength drift," and optically detect intensities of electromagnetic radiation to determine concentrations of one or more gases.

Although in the above description, "fractional pixel shifts" have been explained with respect to shifts of spectral data wherein the shifts have a precision smaller than a sensor pixel in a dispersive spectrometer system, this is not intended to be limiting. For example, a system based upon a transform, such as Hadamard or Fourier transforms, may implement adjustments of spectral data (e.g., reference spectral data, test spectral data, etc.) with a precision smaller than a resolution element of the transform used by the system. Further, such systems may determine the adjustments based on an on-road measurement of the pollutant gas of interest in the exhaust of a passing vehicle.

Other embodiments, uses and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A system for remotely sensing a concentration of a gas in an exhaust plume emitted by a vehicle, wherein the gas absorbs electromagnetic radiation with a wavelength that falls within a wavelength absorption band, the system comprising:
   a spectrometer that comprises a sensor made up of an array of sensor pixels, wherein the spectrometer receives electromagnetic radiation that has traveled along an optical path, the electromagnetic radiation including electromagnetic radiation with a wavelength that falls within a wavelength absorption band of a gas present in an exhaust plume of a passing vehicle, the spectrometer spatially arranging the electromagnetic radiation by wavelength into a spectrum that is incident on the sensor, and wherein each sensor pixel generates an output signal based on an intensity of a portion the electromagnetic radiation that is incident thereon;
   a storage module that stores a scale that associates each sensor pixel with a wavelength range, wherein the wavelength range associated with each sensor pixel is a prediction of the wavelength range of the spectrum of electromagnetic radiation that will be incident on that particular sensor pixel; and
   a scale module that (i) that determines an offset amount of wavelength drift in the spectrometer based on spectral data derived from the output signals generated by the sensor pixels while an exhaust plume of a passing vehicle is in the optical path, and (ii) adjusts for the determined wavelength drift by shifting the scale by the offset amount, wherein the offset amount includes a fractional pixel offset amount.

2. The system of claim 1, further comprising a concentration module that determines the concentration of a gas in an exhaust plume of a passing vehicle based on values of the output signals generated by the sensor pixels while the exhaust plume is in the optical path and the scale.

3. The system of claim 1, wherein the scale module compares the spectral data derived from the output signals generated by the sensor pixels when an exhaust plume of a passing vehicle is present in the optical path with a plurality of sets of reference spectral data to determine a closest match to the derived spectral data from among the plurality of sets of reference spectral data, wherein each of the sets of reference spectral data corresponds to an offset amount of wavelength drift, and wherein the scale module determines the offset amount of wavelength drift to be the offset amount that corresponds to the set of reference spectral data that is the closest match to the derived spectral data.

4. The system of claim 3, wherein the plurality of sets of reference spectral data are determined based on a plurality of sets of stored spectral data that are stored at the storage module.

5. The system of claim 4, wherein the sets of stored spectral data are predetermined using a reference function that reflects an expected shape of one or more absorption dips in the electromagnetic radiation incident on the sensor pixels within a wavelength absorption band of a gas present in an exhaust plume of a passing vehicle.

6. The system of claim 1, wherein the scale module determines the offset amount of wavelength drift, in part, by shifting a set of reference spectral data from an initial alignment to a modified alignment, wherein the set of reference spectral data at the initial alignment is a prediction of the shape of the derived spectral data based on (i) the stored scale and (ii) an expected shape of the derived spectral data within the absorption band of the gas, and wherein the modified alignment substantially aligns the set of reference spectral data with the derived spectral data.

7. The system of claim 6, wherein the amount by which the reference spectral data is shifted between the initial alignment and the modified alignment is substantially proportional to the offset amount of wavelength drift in the spectrometer.

8. A method of remotely sensing a concentration of a gas in an exhaust plume emitted by a vehicle, wherein the gas absorbs electromagnetic radiation with a wavelength that falls within a wavelength absorption band, the method comprising:
   receiving electromagnetic radiation that has traveled along an optical path, the electromagnetic radiation including electromagnetic radiation with a wavelength that falls within a wavelength absorption band of a gas present in an exhaust plume of a passing vehicle;
   spatially arranging the electromagnetic radiation by wavelength into a spectrum that is incident on an array of sensor pixels, wherein each sensor pixel generates an output signal based on an intensity of a portion of the electromagnetic radiation that is incident thereon;
   storing a scale that associates each sensor pixel with a wavelength range, wherein the wavelength range associated with each sensor pixel is a prediction of the wavelength range of the spectrum of electromagnetic radiation that will be incident on that particular sensor pixel;
   determining an offset amount of wavelength drift based on spectral data derived from the output signals generated by the sensor pixels while an exhaust plume of a passing vehicle is in the optical path; and
   adjusting for wavelength drift of the offset amount by shifting the scale by the offset amount, wherein the offset amount includes a fractional pixel offset amount.

9. The method of claim 8, further comprising determining the concentration of a gas in an exhaust plume of a passing vehicle based on values of the output signals generated by the sensor pixels while the exhaust plume is in the optical path and the scale.

10. The method of claim 8, wherein determining the offset amount of the wavelength drift comprises comparing the spectral data derived from the output signals generated by the sensor pixels when an exhaust plume of a passing vehicle is present in the optical path with a plurality of sets of reference spectral data to determine a closest match to the derived spectral data from among the plurality of sets of reference spectral data, wherein each of the sets of reference spectral data corresponds to an offset amount of wavelength drift, and wherein the offset amount of wavelength drift is the offset amount that corresponds to the set of reference spectral data that is the closest match to the derived spectral data.

11. The method of claim 10, wherein determining the offset amount of the wavelength drift further comprises determining the plurality of sets of reference information based on a plurality of sets of stored spectral data.

12. The method of claim 11, wherein the sets of stored spectral data are predetermined using a reference function that reflects an expected shape of an absorption dip in the electromagnetic radiation incident on the sensor pixels within a wavelength absorption band of a gas present in an exhaust plume of a passing vehicle.

13. The method of claim 8, wherein determining the offset amount of wavelength drift comprises shifting a set of reference spectral data from an initial alignment to a modified alignment, wherein the set of reference spectral data at the initial alignment is a prediction of the shape of the derived spectral data based on (i) the stored scale and (ii) an expected shape of the derived spectral data within an absorption band of a gas present in an exhaust plume of a passing vehicle, and wherein the modified alignment substantially aligns the set of reference spectral data with the derived spectral data.

14. The method of claim 8, wherein the amount by which the reference spectral data is shifted between the initial alignment and the modified alignment is substantially proportional to the offset amount of wavelength drift in the spectrometer.

15. A system for remotely sensing a concentration of a gas in an exhaust plume emitted by a vehicle, wherein the gas absorbs electromagnetic radiation with a wavelength that falls within a wavelength absorption band, the system comprising:
   a spectrometer that comprises a sensor made up of an array of sensor pixels, wherein the spectrometer receives electromagnetic radiation that has traveled along an optical path, the electromagnetic radiation including electromagnetic radiation with a wavelength that falls within a wavelength absorption band of a gas present in an exhaust plume of a passing vehicle, the spectrometer spatially arranging the electromagnetic radiation by wavelength into a spectrum that is incident on the sensor, and wherein each sensor pixel generates an output signal based on an intensity of a portion of the electromagnetic radiation that is incident thereon;
   a storage module that stores a plurality of scales and a plurality of sets of reference values that correspond to the scales,
   wherein each scale associates the sensor pixels with predetermined wavelength ranges, the wavelength range associated with each sensor pixel by a given scale being a prediction of the wavelength range of the spectrum of electromagnetic radiation that will be incident on that particular sensor pixel for the given scale, and
   wherein each set of reference values are related to expected values of the output signals generated by the sensor pixels while the exhaust plume of the passing vehicle is present in the optical path, based on the wavelength ranges associated with the sensor pixels by a scale that corresponds to that particular set of reference values;
   a shift module that compares the sets of reference values with a set of signal values of the output signals that are generated by the sensor pixels while the exhaust plume of the passing vehicle is present in the optical path in order to determine which set of reference values most closely correlates with the signal values that are generated while the exhaust plume of the passing vehicle is present in the optical path; and
   an adjustment module that adjusts a current scale to substantially match the scale that corresponds to the set of reference values that most closely correlates with the signal values that are generated while the exhaust plume of the passing vehicle is present in the optical path, wherein the current scale is presently implemented in determining the concentration of the gas based on the output signals.

16. The system of claim 15, wherein the reference values are determined based on a spectrum function that describes an expected value of a sensor pixel as a function of the wavelength range associated with the sensor.

17. A system for remotely sensing a concentration of a gas in an exhaust plume emitted by a vehicle, wherein the gas absorbs electromagnetic radiation with a wavelength that falls within a wavelength absorption band, the system comprising:
   a spectrometer that comprises a sensor made up of an array of sensor pixels, wherein the spectrometer receives electromagnetic radiation that has traveled along an optical path, the electromagnetic radiation including electromagnetic radiation with a wavelength that falls within a wavelength absorption band of a gas present in an exhaust plume of a passing vehicle, the spectrometer spatially arranging the electromagnetic radiation by wavelength into a spectrum that is incident on the sensor, and wherein each sensor pixel generates an output signal based on an intensity of a portion the electromagnetic radiation that is incident thereon; and
   a processor that calibrates the system based on the output signals generated by the sensor pixels while the exhaust plume of the passing vehicle is present in the optical path,
   wherein the calibration of the system corrects for wavelength drift in the spectrometer.

18. A system for remotely sensing a concentration of a gas in an exhaust plume emitted by a vehicle, wherein the gas absorbs electromagnetic radiation with a wavelength that falls within one or more wavelength absorption bands, the system comprising:
   a spectrometer that comprises a sensor made up of an array of sensor pixels, wherein the spectrometer receives electromagnetic radiation that has traveled along an optical path, the electromagnetic radiation including electromagnetic radiation with a wavelength that falls within one or more wavelength absorption bands of a gas present in an exhaust plume of a passing vehicle, the spectrometer spatially arranging the electromagnetic radiation by wavelength into a spectrum that is incident on the sensor, and wherein each sensor pixel generates an output signal based on an intensity of a portion the electromagnetic radiation that is incident thereon; and
   a processor that performs a peak-match between one or more output signals generated by sensor pixels that receive a portion of the spectrum created by the spectrometer while the exhaust plume of the passing vehicle is in the optical path and one or more sets of reference spectral data to determine a wavelength drift offset of the spectrometer, wherein the processor further determines the concentration of the gas in the exhaust plume of the passing vehicle based on the one or more output signals generated by the sensor pixels that receive a portion of the spectrum created by the spectrometer while the exhaust plume of the passing vehicle is in the optical path, and wherein the determination of the concentration of the gas made by the processor is corrected for the wavelength drift offset determined by the processor.

19. The system of claim 18, wherein the one or more sets of reference spectral data comprise predetermined, stored sets of spectral data.

* * * * *